US010945607B2

(12) United States Patent
Sato (10) Patent No.: US 10,945,607 B2
(45) Date of Patent: Mar. 16, 2021

(54) SPECTROSCOPE, OPTICAL INSPECTION DEVICE AND OCT DEVICE (71) Applicant: HORIBA, Ltd., Kyoto (JP)

(72) Inventor: Seichi Sato, Kyoto (JP)

(73) Assignee: HORIBA, LTD., Kyoto (JP)

(*) Notice: Subject to any disclaimer, the term of this patent is extended or adjusted under 35 U.S.C. 154(b) by 340 days.

(21) Appl. No.: 15/781,630

(22) PCT Filed: Dec. 13, 2016

(86) PCT No.: PCT/JP2016/087062
§ 371 (c)(1),
(2) Date: Jun. 5, 2018

(87) PCT Pub. No.: WO2017/104661
PCT Pub. Date: Jun. 22, 2017

(65) Prior Publication Data
US 2020/0260959 A1     Aug. 20, 2020

(30) Foreign Application Priority Data
Dec. 15, 2015 (JP) .............. JP2015-244658

(51) Int. Cl.
A61B 5/00      (2006.01)
G01J 3/02      (2006.01)
G01J 3/10      (2006.01)
G01J 3/18      (2006.01)
G02B 27/42     (2006.01)
(Continued)

(52) U.S. Cl.
CPC .......... A61B 5/0066 (2013.01); A61B 5/0075 (2013.01); G01J 3/0208 (2013.01);
(Continued)

(58) Field of Classification Search
CPC ............... A61B 5/0066; A61B 5/0075; A61B 2029/3614; A61B 3/102; A61B 3/1225;
(Continued)

(56) References Cited

U.S. PATENT DOCUMENTS 5,272,550 A * 12/1993 Dickson .............. G02B 5/3025
                                                   359/15
5,657,306 A *  8/1997 Komatsu ............. G11B 7/1356
                                                   369/112.19
(Continued)

FOREIGN PATENT DOCUMENTS

EP    2617351 A       7/2013
JP    2005533249 A   11/2005
(Continued)

OTHER PUBLICATIONS

Extended European Search Report dated Jun. 17, 2019 issued for corresponding European patent application No. 16 875 638.5 (7 pages).
(Continued)

Primary Examiner — Rochelle D Turchen
Assistant Examiner — Chao Sheng
(74) Attorney, Agent, or Firm — Lucas & Mercanti, LLP (57) ABSTRACT This invention is to provide a spectroscope that can improve resolution and reduce loss of light intensity and/or distortion of a wave front while enabling detection of the optical spectrum for each of a plurality of polarization components in incident light. The spectroscope is a spectroscope that comprises a first diffraction grating 51 to which at least a transmitted light or a reflected light from an object to be measured enters, which diffracts a first polarization component of the incident light and which transmits a second polarization component that is different from the first polarization component of the incident light without diffraction, and a first light-receiving element 55 that receives a spectrum of the light diffracted by the first diffraction grating 51.

10 Claims, 8 Drawing Sheets (51) Int. Cl.
*G01J 3/12* (2006.01)
*A61B 90/00* (2016.01)
*A61B 3/10* (2006.01)
*A61B 3/12* (2006.01)

(52) U.S. Cl.
CPC ........... *G01J 3/0218* (2013.01); *G01J 3/0224* (2013.01); *G01J 3/108* (2013.01); *G01J 3/18* (2013.01); *G02B 27/4261* (2013.01); *A61B 3/102* (2013.01); *A61B 3/1225* (2013.01); *A61B 5/0088* (2013.01); *A61B 2090/3614* (2016.02); *A61B 2562/0233* (2013.01); *G01J 2003/1291* (2013.01); *G01J 2003/1861* (2013.01)

(58) Field of Classification Search
CPC .. A61B 5/0088; A61B 2526/0233; G01J 3/18; G01J 3/0208; G01J 3/0218; G01J 3/108; G01J 2003/1291; G01J 2003/1861; G02B 27/4261

See application file for complete search history.

(56) References Cited

U.S. PATENT DOCUMENTS

| | | |
|---|---|---|
| 2007/0038040 A1 | 2/2007 | Cense et al. |
| 2012/0120408 A1 | 5/2012 | Yasuno et al. |
| 2012/0327412 A1 | 12/2012 | Amako |
| 2013/0107272 A1 | 5/2013 | Hirose |
| 2015/0355023 A1 | 12/2015 | Ota |

FOREIGN PATENT DOCUMENTS

| | | |
|---|---|---|
| JP | 2013007830 A | 1/2013 |
| JP | 2014232103 A | 12/2014 |
| WO | 2004008089 A1 | 1/2004 |

OTHER PUBLICATIONS

International Search Report dated Feb. 28, 2017 for PCT/JP2016/087062 and English translation.

* cited by examiner

SPECTROSCOPE, OPTICAL INSPECTION DEVICE AND OCT DEVICE

CROSS REFERENCE TO RELATED APPLICATION

This Application is a 371 of PCT/JP2016/087062 filed on Dec. 13, 2016, which, in turn, claimed the priority of Japanese Patent Application No. JP 2015-244658 filed on Dec. 15, 2015, both applications are incorporated herein by reference.

FIELD OF THE ART

This invention relates to an OCT device that is so configured to enable measurement of an optical spectrum of interference light wherein a reflected light from an object to be measured and a reference light interfere each other in order to obtain a tomographic image of, for example, the object to be measured.

BACKGROUND ART

In order to make a diagnosis of, for example, a state of a retina in a short time, a tomographic image of the retina is taken by the use of the OCT device.

The OCT device is so configured that an optical system irradiates a near infrared light on the retina and interferes with the reference light and the reflected light from the retina. Then the obtained interference light is spectrally dispersed by a diffraction grating and the optical spectrum is detected by a light-receiving element. Furthermore, a tomographic image of the retina is produced based on the optical spectrum.

Figure 8:
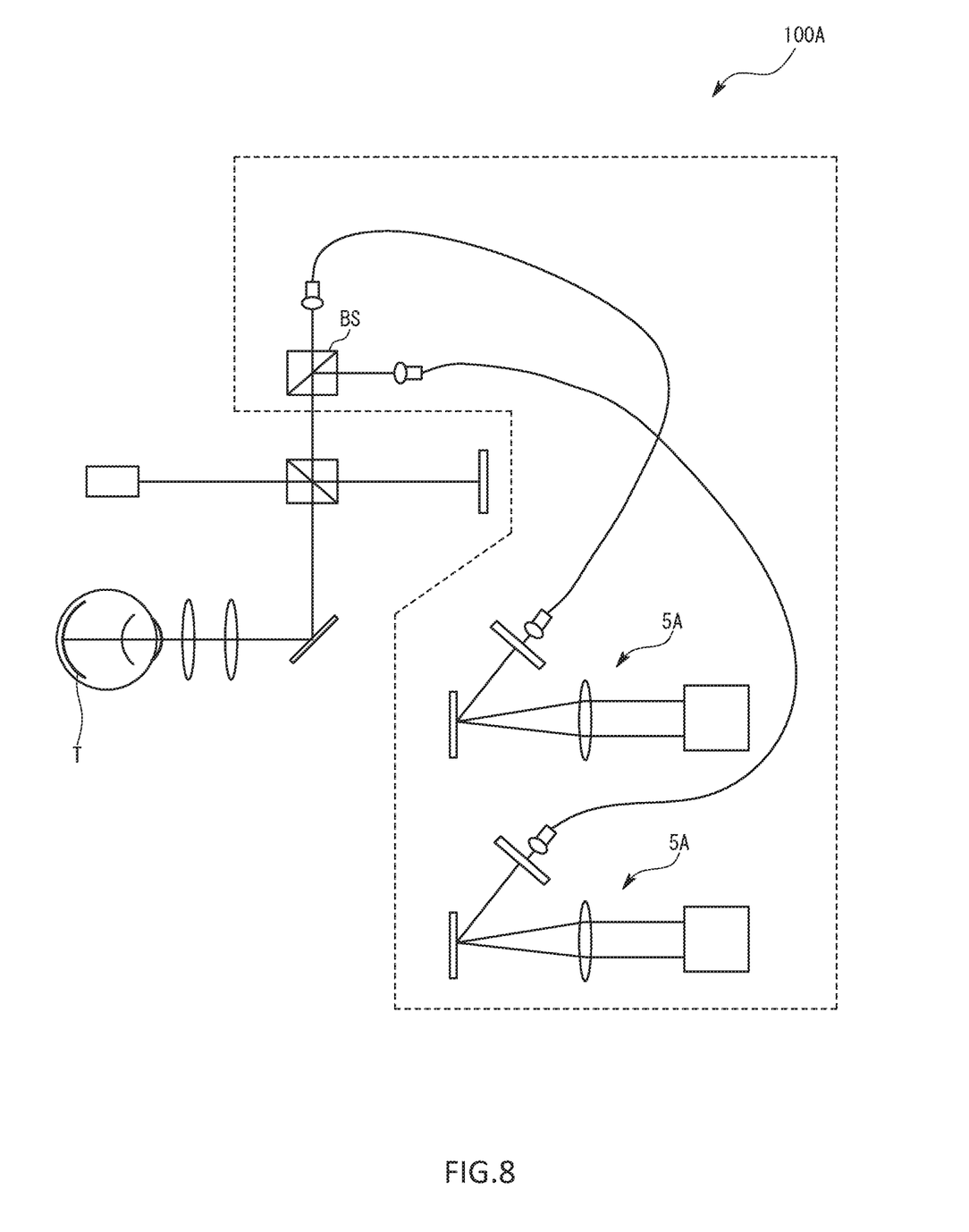
FIG. 8 is a pattern view showing a conventional OCT device.

As shown in a patent document 1 or FIG. 8, some of the OCT device 100A is provided with a spectroscope that separates the interference light into two optical paths 5A, 5B each having a TE polarization component and a TM polarization component respectively by a polarization beam splitter (BS) and the optical spectrum is obtained for each of the polarization components. With this arrangement, it is expected that a more minute medical diagnosis can be conducted on the lesion based on a difference in the tomographic image of the retina (T) produced by each of the polarization components.

However, since the OCT device 100A that can measure the optical spectrum for each of the polarization components of the interference light uses the polarization beam splitter (BS), there is a problem that the OCT device 100A becomes bulky compared with an OCT device that does not split the polarized beam. In addition, a spectroscope used for the above-mentioned OCT device 100A has a problem that a loss of the light intensity or distortion of a wave front resulting from the reflection becomes big because a number of the reflecting surface becomes numerous. This loss of the light intensity or the distortion of the wave front reduces the resolution as the spectroscope.

PRIOR ART DOCUMENTS

Patent Document

Patent document 1: US patent document US2007/0038040

DISCLOSURE OF THE INVENTION

Problems to be Solved by the Invention

The present claimed invention intends to solve all of the problems and a main object of this invention is to provide a spectroscope that can improve resolution and reduce loss of light intensity and/or distortion of a wave front while enabling detection of the optical spectrum for each of a plurality of polarization components in incident light.

Means to Solve the Problems

More specifically, the spectroscope in accordance with this invention is a spectroscope that comprises a first diffraction grating to which at least a transmitted light or a reflected light from an object to be measured enters, which diffracts a first polarization component of the incident light and which transmits a second polarization component that is different from the first polarization component of the incident light without diffraction, and a first light-receiving element that receives a spectrum of the light diffracted by the first diffraction grating.

A concept of "diffracts a first polarization component of the incident light" includes not only a case that all of the first polarization component of the incident light is diffracted by the first diffraction grating but also a case that at least a ratio of the first polarization component of the incident light that is diffracted by the first diffraction grating is bigger than a ratio of the first polarization component of the incident light that is transmitted through the first diffraction grating without diffraction.

In addition, a concept of "transmits a second polarization component without diffraction" includes not only a case that all of the second polarization component of the incident light is transmitted through the first diffraction grating without diffraction but also a case that at least a ratio of the second polarization component of the incident light that is transmitted through the first diffraction grating without diffraction is bigger than a ratio of the second polarization component of the incident light that is diffracted by the first diffraction grating.

In accordance with this arrangement, it is possible for the first diffraction grating to separate the incident light into the first polarization component and the second polarization component and to spectrally disperse the first polarization component of the incident light at the same time and it is possible for the first light-receiving element to obtain an optical spectrum.

Accordingly, since there is no need of providing a polarization beam splitter to split the incident light into each polarization component, it is possible not to increase loss of the light intensity on the reflecting surface or distortion of the wave front without increasing a number of the reflecting surface. As a result of this, the spectroscope can obtain high resolution while obtaining the spectrum for each polarization component. In addition, in accordance with the spectroscope having this arrangement, it becomes possible to constitute an optical inspection device of an OCT device having more accurate examination precision based on a plurality of polarization components without increasing a size of the device.

In order to simplify an arrangement of the optical system while making it possible to obtain the optical spectrum of the second polarization component of the light that is transmitted through the first diffraction grating without diffraction, the spectroscope may further comprise a second diffraction grating that is arranged to enter the light transmitted through the first diffraction grating without diffraction and that diffracts the second polarization component of the light that is transmitted through the first diffraction grating, and a second light-receiving element that receives a spectrum of the light diffracted by the second diffraction grating.

In order to make it possible both to arrange the first diffraction grating and the second diffraction grating in parallel and to facilitate arranging the first light-receiving element and the second light-receiving element, each of the first diffraction grating and the second diffraction grating may be a transmission type diffraction grating.

In order to make it possible to condense each polarization components of the light diffracted by the first diffraction grating and the second diffraction grating so as to measure each optical spectrum in a predetermined range and to downsize the spectroscope having the first light-receiving element and the second light-receiving element, the spectroscope may further comprise a first lens arranged between the first diffraction grating and the first light-receiving element, and a second lens arranged between the second diffraction grating and the second light-receiving element.

In order to make it possible to make a value of a distance between gratings or a value of a depth of a groove of a grating of the first diffraction grating easy to manufacture so as to enhance manufacturability, the first polarization component may be a TM polarization component and the second polarization component may be a TE polarization component.

In order to produce a data that is useful to obtain a state or a characteristic of an object to be measured based on the polarization component resulting from the transmitted light or the reflected light from the object to be measured, an optical inspection device that comprises the spectroscope in accordance with this invention and a spectrum signal output part that outputs a spectrum signal indicating a distribution for each wavelength based on at least an output signal of the first light-receiving element may be used.

As a concrete arrangement that is appropriate for obtaining a tomographic image of an organism in order to inspect the organism such as a retina of an eye or a tooth represented is an OCT device that comprises the optical inspection deice in accordance with this invention, an optical fiber mechanism wherein the light that enters from a light incident end is emitted from a light emission end to the first diffraction grating, a light source that emits a near infrared light, a diverging mechanism that diverges the light emitted from the light source into a measurement light and a reference light, a reference optical system that enters the reference light diverged by the diverging mechanism to the light incident end and a measurement optical system that irradiates the measurement light diverged by the diverging mechanism on the object to be measured so as to enter the reflected light that generates on the object to be measured.

In order to make it easier to visually grasp a lesion that has been difficult to find in case of conducting an image diagnosis on an object to be measured, the OCT device may further comprise an analysis part that produces a first tomographic image based on an output from the first light-receiving element and produces a second tomographic image based on an output from the second light-receiving element.

Effect of the Invention

In accordance with the spectroscope in accordance with this invention, it is possible for the first diffraction grating to separate the incident light into the first polarization component and the second polarization component and to diffract and spectrally disperse the first polarization component of the incident light. As a result of this, unlike a conventional spectroscope, since there is no need of additionally providing a polarization beam splitter to separate the polarization component, it is possible to reduce loss of light intensity or distortion of a wave surface without increasing a number of a reflecting surface.

EXPLANATION OF CODES

100 . . . OCT device
1 . . . light source
2 . . . diverging mechanism
3 . . . measurement optical system
31 . . . reflecting mirror
32 . . . lens
4 . . . reference optical system
41 . . . reference mirror
5 . . . interference optical system
5F . . . optical fiber mechanism
IN . . . incident end
FB . . . fiber part
EX . . . emission end
51 . . . first diffraction grating
52 . . . second diffraction grating
53 . . . first condensing lens
54 . . . second condensing lens
55 . . . first light-receiving element
56 . . . second light-receiving element

EMBODIMENTS OF THE INVENTION

Figure 1:
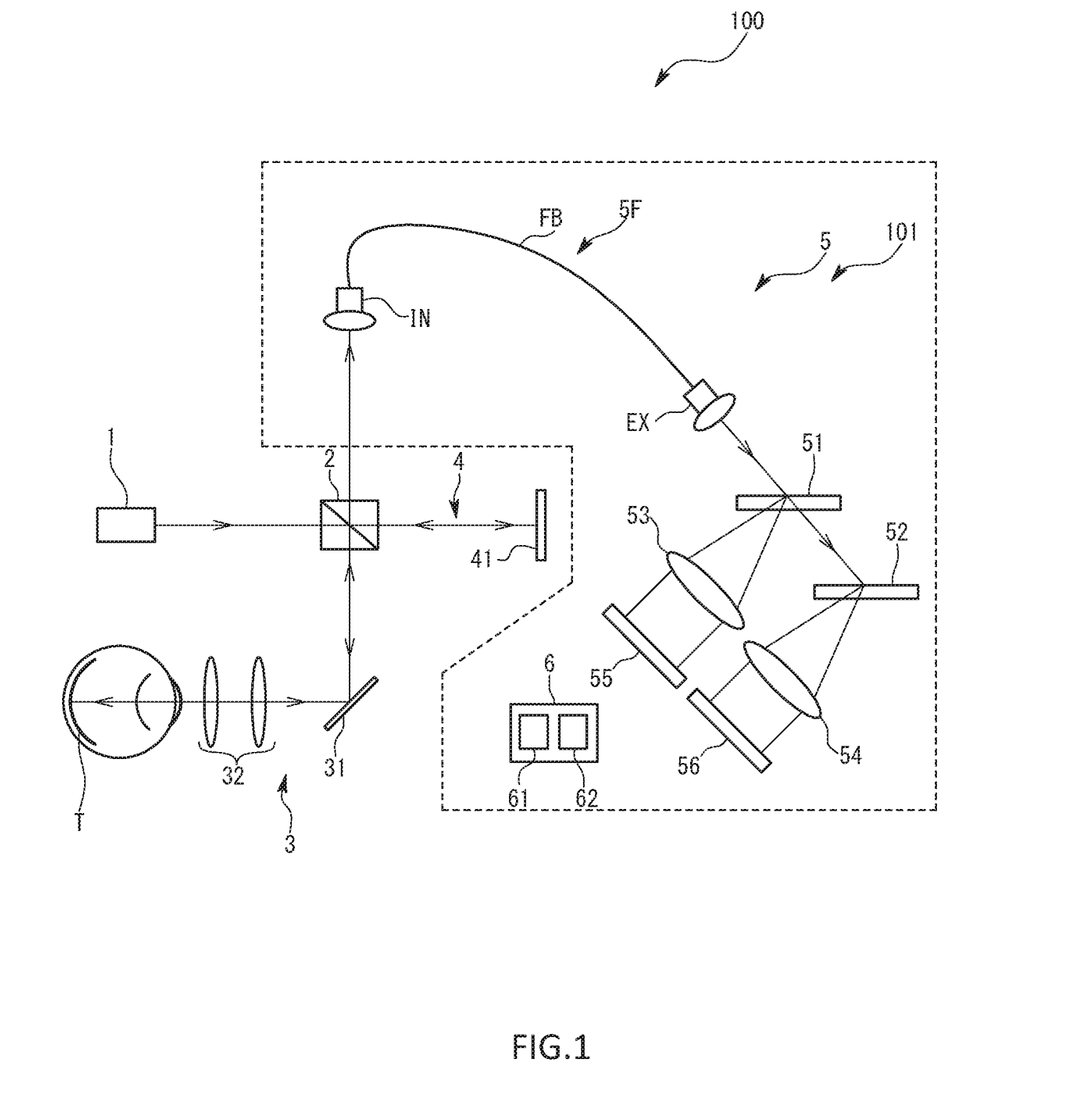
FIG. 1 is a pattern diagram showing an OCT device in accordance with a first embodiment of this invention.

An OCT (Optical Coherence Tomography) device 100 in accordance with a first embodiment of this invention is used for imaging a tomographic image of a retina (T) in an eyeball as an object to be measured in a department of ophthalmology. The OCT device 100 is polarization sensitive and comprises, as shown in FIG. 1, a light source 1, a diverging mechanism 2, a measurement optical system 3, a reference optical system 4, a spectroscope 101 constituting an interference optical system 5 and an arithmetic mechanism 6.

The light source 1 emits low coherence light of a near infrared wavelength. In this embodiment, the light source 1 emits a near infrared light of, for example, 1100 nm wavelength.

The diverging mechanism 2 is a half mirror 2 arranged diagonally to an optical axis of the light source 1. The light that is reflected by the half mirror 2 among the light emitted from the light source 1 enters the measurement optical system 3 as a measurement light. The light that is transmitted through the half mirror 2 among the light emitted from the light source 1 enters the reference optical system 4 as a reference light.

The measurement optical system 3 comprises at least a reflecting mirror 31 and a plurality of lenses 32, and irradiates the measurement light on the retina (T) as being the object to be measured. In addition, the measurement optical system 3 introduces the reflected light on the retina (T) into the half mirror 2.

The reference optical system 4 comprises at least a reference mirror 41, and introduces the reference light into the half mirror 2.

The reflected light introduced into the half mirror 2 penetrates into the half mirror 2 and goes straight ahead, and the reference light is reflected by the reflecting mirror 31 and joins the reflected light. As a result of this, after passing the half mirror 2, the reflected light on the retina (T) and the reference light become the interference light and interfere each other and then enter the interference optical system 5.

Figure 2:
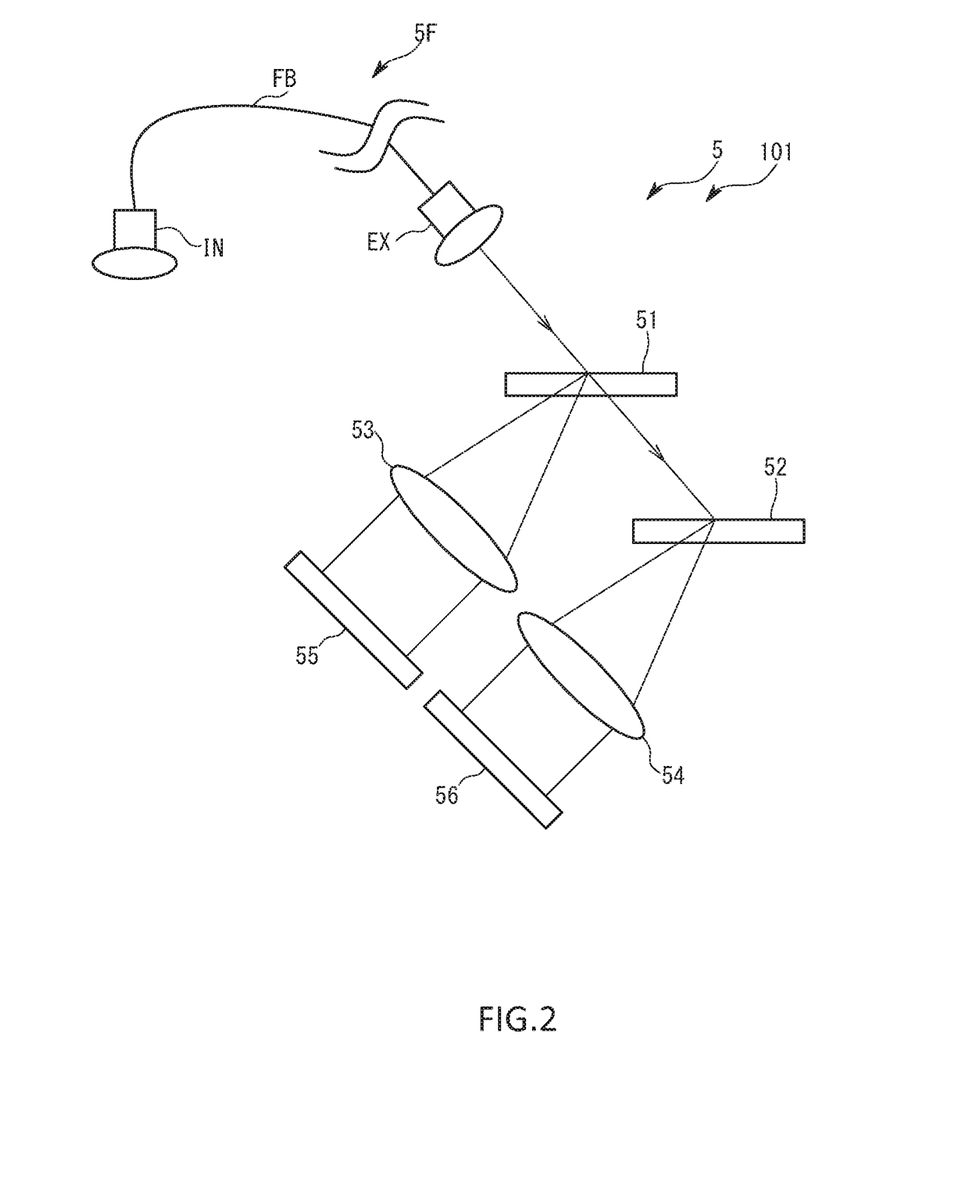
FIG. 2 is an enlarged pattern diagram showing an interference optical system in this embodiment.

The interference optical system 5 as being the spectroscope 101 comprises, as shown by the enlarged view in FIG. 2, comprises an optical fiber mechanism 5F, a first diffraction grating 51, a first condensing lens 53, a first light-receiving element 55, a second diffraction grating 52, a second condensing lens 54 and a second light-receiving element 56.

The optical fiber mechanism 5F comprises an incident end (IN) into which the interference light enters, a fiber part (B) by which waves of the interference light are guided and an emission end (EX) through which the collimated interference light obliquely enters a surface where a grating of the first diffraction grating 51 is formed. The lens may be a single lens, or may be a doublet lens or a triplet lens, or combination of the doublet lens and the triplet lens.

Figure 3:
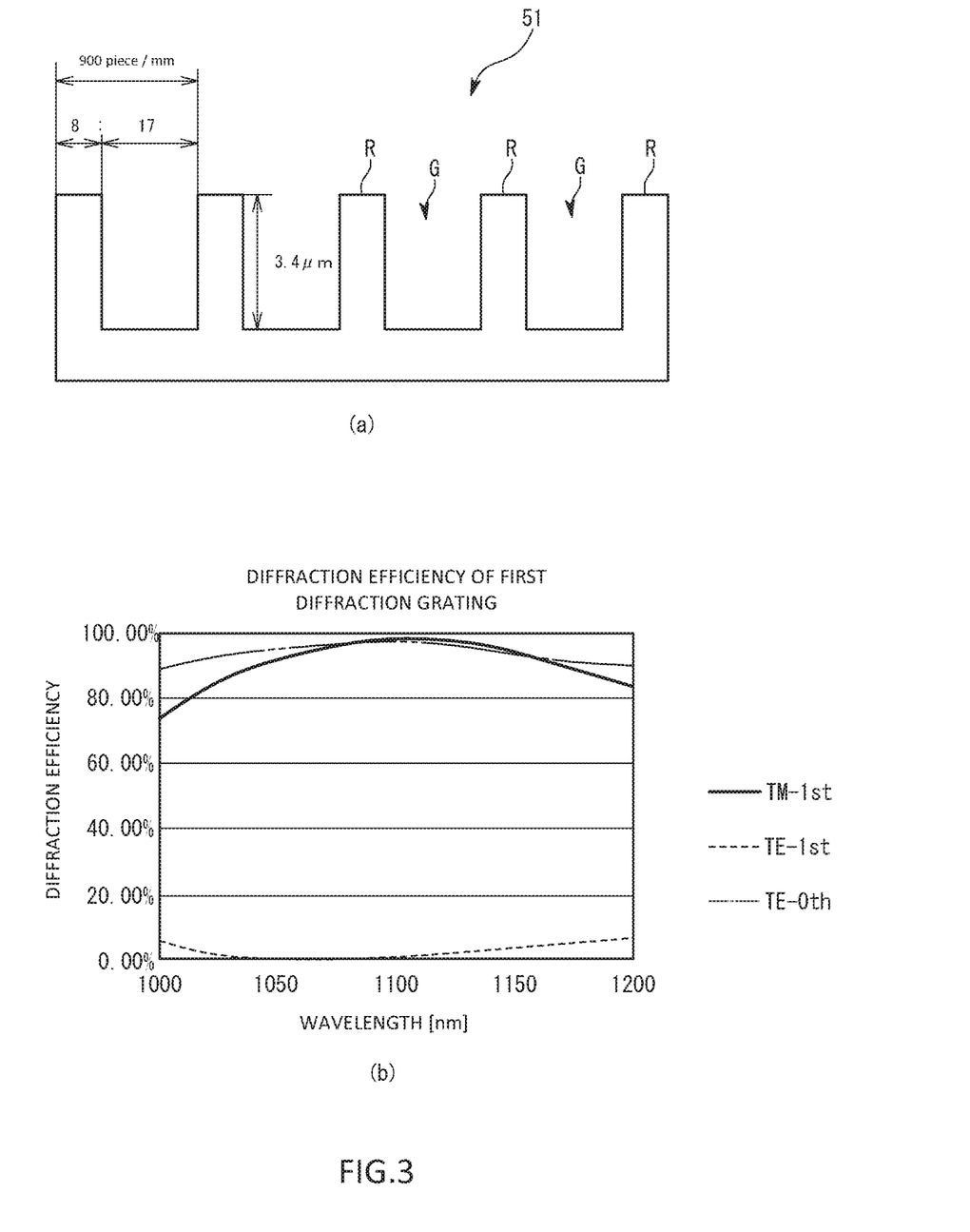
FIG. 3 is a pattern diagram and a graph showing a characteristic of a first diffraction grating in the first embodiment.

The first diffraction grating 51 is a binary type diffraction grating and is so configured to diffract a TM polarization component (s polarization component) as a first polarization component of the interference light and to transmit a TE polarization component (p polarization component) without diffraction 23s a second polarization component of the interference light. In this embodiment, in order to make it possible to selectively diffract or transmit the light having a wave length of 1100 nm for each of the polarization components, as shown in FIG. 3(a), the first diffraction grating 51 is made of a grating that is formed on a surface plate part on a plate-shaped synthetic quartz by forming a ridge part (R) projecting viewed from a direction perpendicular to a paper surface and a groove (G) penetrating in the direction perpendicular to the paper in turn. A size or a shape of the ridge part (R) and the groove (G) may be appropriately set in accordance with a wavelength of the incident light. A width of the ridge part (R) is made smaller than a width of the groove (G) for the first diffraction grating 51. In the first embodiment, an object to be diffracted for the first diffraction grating 51 is the TM polarization component of the light having a wavelength of near 1100 nm, and the grating is formed with a marking density of 900 piece/mm so as to make a ratio of the width of the ridge part (R) to the width of the groove (G) 8:17 (duty ratio 0.32). In addition, a depth of the groove (G) of the first diffraction grating 51 is formed to be 3.4 µm. It is possible to differentiate an amount of the diffraction for each polarization component of the interference light by adjusting the above-mentioned duty ratio and the depth of the groove (G). In addition, since the grating is formed as mentioned above, the diffraction efficiency of the first diffraction grating 51 for each polarization component is shown by a graph in FIG. 3 (b). More specifically, the first diffraction grating 51 is formed as the transmitting type diffraction grating having polarization dependency.

The first condensing lens 53 is arranged so as to condense and collimate the TM polarization component of the interference light diffracted by the first diffraction grating 51. The first condensing lens 53 may be a single lens, or may be a doublet lens comprising two lenses or a triplet lens comprising three lenses. In addition, the first condensing lens 53 may be a combination of the doublet lens and the triplet lens.

The first light-receiving element 55 is a line sensor extending in a spectral direction of the interference light, and is arranged in a diffraction direction of the TM polarization component of the interference light of the first diffraction grating 51 viewed from the first diffraction grating 51. More specifically, the optical spectrum of the TM polarization component of the interference light is measured by the first light-receiving element 55.

Figure 4:
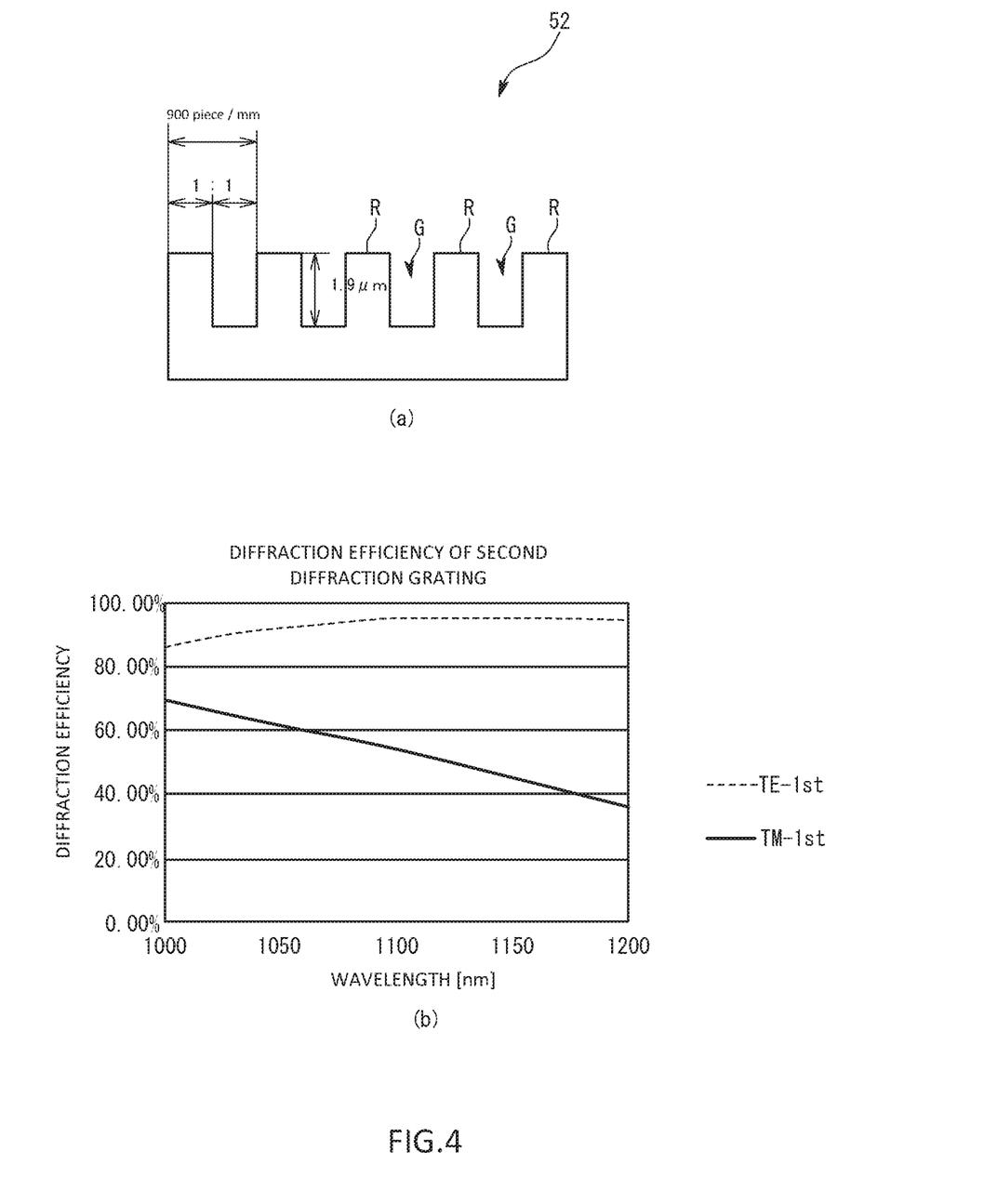
FIG. 4 is a pattern diagram and a graph showing a characteristic of a second diffraction grating in the first embodiment.

The second diffraction grating 52 is a binary type diffraction grating made of plate-shaped synthetic quartz wherein a shape of a grating is different from that of the grating of the first diffraction grating 51. The second diffraction grating 52 is, as shown in FIG. 2, arranged in the transmitting direction of the TE polarization component of the interference light from the first diffraction grating 51 viewed from the first diffraction grating 51. In addition, the second diffraction grating 52 is arranged so that a surface plate part on which the grating of the diffraction grating 52 is formed is in parallel to the surface plate part of the first diffraction grating 51. More specifically, the incident angle of the interference light entering the first diffraction grating 51 is made to be equal to the incident angle of the interference light entering the second diffraction grating 52. In the first embodiment, the object to be diffracted for the second diffraction grating 52 is the TE polarization component for the light having a wavelength of near 1100 nm, and as shown in FIG. 4(a), the grating is formed with a marking density of 900 piece/mm so as to make a ratio of the width of the ridge part (R) to the width of the groove (G) 1:1 (duty ratio 0.5). In addition, the depth of the groove (G) of the second diffraction grating 52 is formed to be shallower than the depth of the groove (G) of the first diffraction grating 51 and is set to be 1.9 µm. The diffraction efficiency of the second diffraction grating 52 for each polarization component is shown by a graph in FIG. 4 (b). More specifically, the second diffraction grating 52 is formed as the diffraction grating of transmitting type having lower polarization dependency compared with the first diffraction grating 51.

The second condensing lens 54 is arranged so as to condense and collimate the TE polarization component of the interference light diffracted by the second diffraction grating 52. The second condensing lens 54 may be a single lens, or may be a doublet lens comprising two lenses or a triplet lens comprising three lenses. In addition, the second condensing lens 54 may be a combination of the doublet lens and the triplet lens.

Similar to the first light-receiving element 55, the second light-receiving element 56 is also a line sensor extending in the spectral direction of the interference light and is arranged in the diffraction direction of the TE polarization component of the interference light from the second diffraction grating 52 viewed from the second diffraction grating 52. The optical spectrum of the TE polarization component of the interference light is measured by the second light-receiving element 56.

The arithmetic mechanism 6 is a so-called computer comprising a CPU, a memory, an A/D converter, a D/A converter and input/output devices, and produces functions as, at least a spectrum signal output part 61 and an analysis part 62 by executing programs for an optical inspection device and programs for an OCT device stored in the memory and by cooperatively working each device. In the first embodiment, the spectrum signal output part 61 outputs a spectrum signal indicating a distribution of each polarization component for each wavelength based on an output signal of the first light-receiving element 55 and the second light-receiving element 56. The analysis part 62 produces a first tomogram image as being a tomogram image of the retina (T) based on the TM polarization component of the interference light based on the output of the first light-receiving element 55, and produces a second tomogram image as being a tomogram image of the retina (T) based on the TE polarization component of the interference light based on the output of the second light-receiving element 56. More concretely, the analysis part 62 calculates reflectance of the light for each depth of the retina (T) based on the spectrum signal of the TM polarization component and the spectrum signal of the TE polarization component output by the spectrum signal output part 61. The light emitted from the light source 1 is scanned on the retina (T) and the spectrum signal for each polarization component is produced for each emitting point. The analysis part 62 accumulates a plurality of spectrum signals of each polarization component obtained by the scan, and calculates the reflectance of each polarization component for each depth of the retina (T). Then, the analysis part 62 produces the first tomography image and the second tomography image based on the information of the reflectance of each polarization component to the depth of the retina (T).

In case that, for example, a lesion occurring in a biological tissue has a polarization dependency of the reflectance, a difference appears between the first tomography image and the second tomography image on a location of the lesion. Accordingly, it becomes possible to diagnose the retina (T) in more detail by outputting the first tomography image and the second tomography image based on each polarization component.

In accordance with the OCT device 100 having this arrangement, as shown in FIG. 3(b), it is possible for the first diffraction grating 51 to diffract most of the TM polarization component of the incident interference light and to transmit the TE polarization component almost without diffraction. Accordingly, it is possible for the first light-receiving element 55 to obtain the optical spectrum of the TM polarization component of the interference light.

In addition, since it is so configured that the interference light that is transmitted through the first diffraction grating 51 and that comprises almost only the TE polarization component enters the second diffraction grating 52, it is possible for the second diffraction grating 52 to diffract the TE polarization component of the interference light and for the second light-receiving element 56 to obtain the optical spectrum of the TE polarization component of the interference light.

As mentioned above, since the first diffraction grating 51 serves as both of a function of separating the interference light into the TM polarization component and the TE polarization component and a function of diffracting only the TM polarization component, unlike the conventional arrangement there is no need of providing a polarization beam splitter in order to obtain the tomographic image for each polarization component and it is possible to omit the polarization beam splitter.

As a result of this, it is possible to downsize whole of the OCT device 100 by reducing a number of the components compared with a conventional arrangement.

In addition, in case that the OCT device 100 is used as the spectroscope 101, while the optical spectrum for two polarization components of the light from the object to be measured can be obtained, it is possible to make a number of the reflecting surface almost the same as that of the conventional one. As this result, loss of the light intensity or distortion of the wave surface can be reduced almost as the same as the conventional arrangement so that it is possible to improve the resolution while obtaining a plurality of polarization components.

Figure 5:
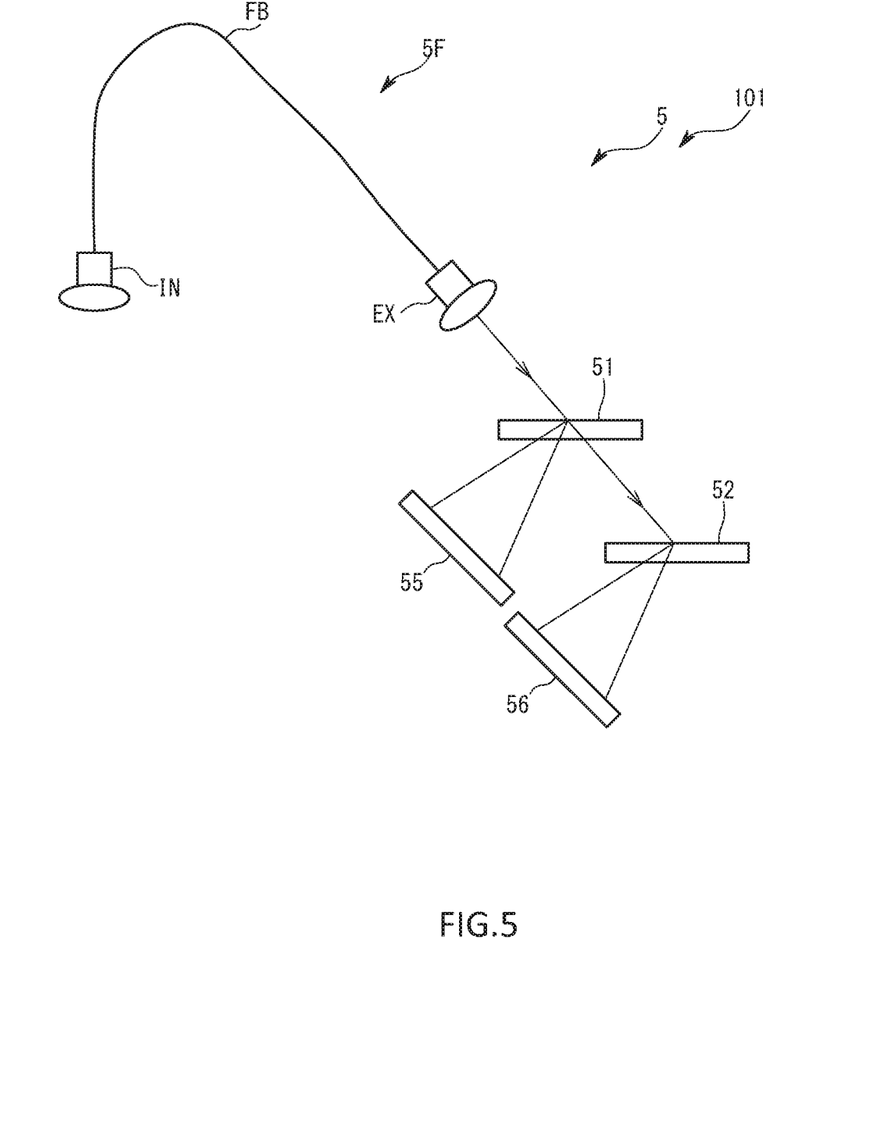
FIG. 5 is a pattern diagram showing an interference optical system of an OCT device in accordance with a second embodiment of this invention.

Next, an OCT device 100 in accordance with a second embodiment of this invention will be explained with reference to FIG. 5. The same parts as those in the second embodiment are denoted by the same reference numerals as those in the first embodiment.

The OCT device 100 of the second embodiment has an interference optical system whose arrangement is different from the interference optical system of the first embodiment. More specifically, as shown in FIG. 5, the OCT device 100 of this second embodiment is not provided with the first condensing lens 53 and the second condensing lens 54 that are provided for the first embodiment, and each of the interference light diffracted by the first diffraction grating 51 and the second diffraction grating 52 directly enters the first light-receiving element 55 and the second light-receiving element 56 respectively.

In accordance with this arrangement, similar to the first embodiment, the optical spectrum can be obtained for each polarization component of the interference light by the first light-receiving element 55 and the second light-receiving element 56 and the tomographic image can be produced based on each optical spectrum. In addition, in accordance with the OCT device 100 of the second embodiment, it is possible to reduce a number of components much more than the OCT device 100 of the first embodiment and to promote downsizing.

Figure 6:
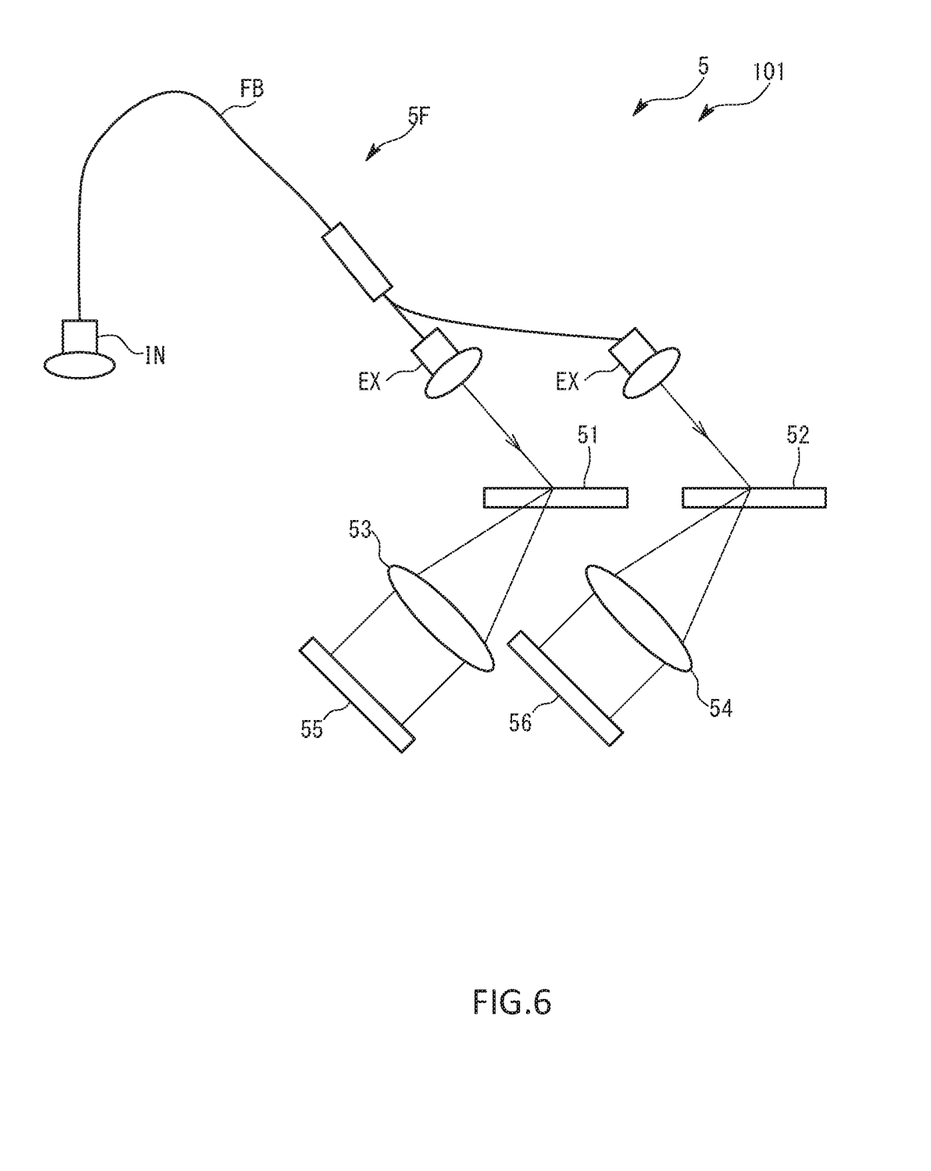
FIG. 6 is a pattern diagram showing an interference optical system of an OCT device in accordance with a third embodiment of this invention.

Next, an OCT device 100 in accordance with a third embodiment of this invention will be explained with reference to FIG. 6. The same parts as those in the third embodiment are denoted by the same reference numerals as those in the first embodiment.

The OCT device 100 of the third embodiment has a structure of an optical fiber mechanism 5F of the interference optical system 5 that is different from that of the above-mentioned embodiment and an arrangement of the second diffraction grating 52 relative to the first diffraction grating 51 that is different from that of the above-mentioned embodiment.

More concretely, the optical fiber mechanism 5F comprises an incident end (IN) into which one interference light enters, a fiber part (FB) that diverges into two in the middle by means of a coupler and exit ends (EX) from which two interference lights exit. More specifically, the interference light is distributed into two exit ends (EX).

Each of the exit ends (EX) is provided with the first diffraction grating 51 and the second diffraction grating 52 respectively, and each of the diffracted interference lights enters the first light-receiving element 55 and the second light-receiving element 56 respectively.

The first diffraction grating 51 has the same structure as that of the first embodiment, and the second diffraction grating 52 diffracts the TE polarization component of the interference light and transmits the TM polarization component of the interference light without diffraction. This is realized by appropriately adjusting the duty ratio and the depth of the groove (G) of the grating formed on the second diffraction grating 52.

In accordance with the OCT device 100 of the third embodiment, since there is no need of providing a polarization beam splitter, it is also possible to downsize whole of the OCT device 100.

An OCT device 100 in accordance with a forth embodiment of this invention will be explained with reference to FIG. 7. The same parts as those in the forth embodiment are denoted by the same reference numerals as those in the first embodiment.

Figure 7:
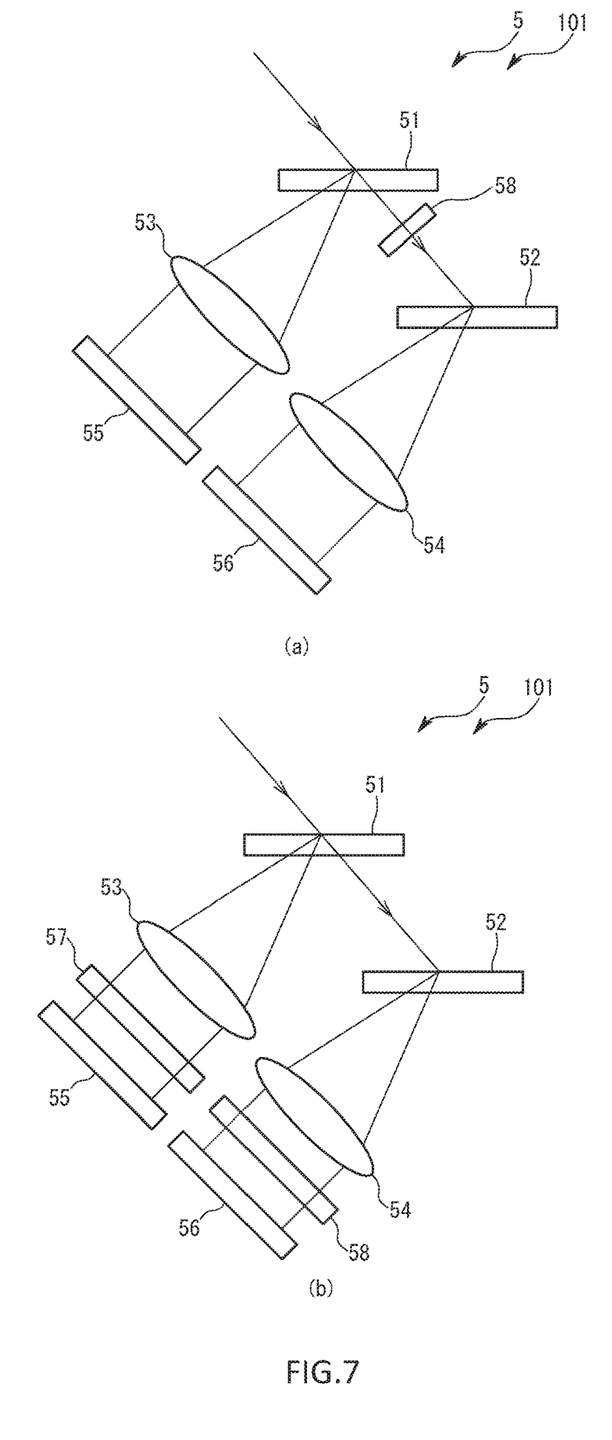
FIG. 7 is a pattern diagram showing an interference optical system of an OCT device in accordance with a forth embodiment of this invention

As shown in FIG. 7 (*a*) and Fig. (b), the interference optical system 5 as being the spectroscope 101 of the forth embodiment further comprises a polarizer. More concretely, between the first diffraction grating 51 and the second diffraction gating 52 in the embodiment shown in FIG. 7 (*a*) provided is a second polarizer 58 that transmits only a second polarization component among the light that is transmitted through the first diffraction grating 53. In accordance with this arrangement, it is possible to prevent the light of the first polarization component that is transmitted through the first diffraction grating 53 without diffraction from reaching the second diffraction grating 54 so that the optical spectrum of each polarization component can be obtained more precisely. In addition, as shown in FIG. 7 (*b*), the first polarizer 57 that transmits only the first polarization component may be provided between the first diffraction grating 51 and the first light-receiving element 55 and the second polarizer 58 may be provided between the second diffraction grating 52 and the second light-receiving element 56. In addition, the first polarizer 57 that transmits only the first polarization component may be provided between the first diffraction grating 51 and the first light-receiving element 55, and the second polarizer 58 that transmits only the second polarization component among the light that is transmitted through the first diffraction grating 53 may be provided between the first diffraction grating 51 and the second diffraction grating 52.

Other embodiment will be explained.

The first diffraction grating and the second diffraction grating are not limited to the transmission type diffraction grating, and may be a reflection type diffraction grating. In addition, the first diffraction grating and the second diffraction grating are not limited to a diffraction grating wherein a ridge part and a groove are formed alternately, and may be a transmission type VPH (Volume Phase Holographic) diffraction grating wherein a refraction factor changes in a sinusoidal state to a face plate direction. Furthermore, the first and the second diffraction gratings may be a diffraction grating wherein a multilayer film comprising a plurality of layers in which adjacent layers have a different refraction factor is formed and a rectangle-shaped or trapezoid-shaped ridge part and a rectangle-shaped or trapezoid-shaped groove are formed alternatingly by etching the multilayer film. Even if the diffraction grating has the above-mentioned arrangement, it is possible to use the diffraction grating as a constitutional element of the spectroscope in accordance with this invention by differentiating the transmittance of the diffraction efficiency for each polarization component.

The first light-receiving element and the second light-receiving element are not limited to the line sensor as being a single dimensional sensor and may be a two dimensional sensor (area sensor). In case of using the two dimensional sensor, it may be so configured that a picture element is made longer in a direction to which the optical spectrum appears. In addition, the first light-receiving element and the second light-receiving element may be comprised by the use of a single line sensor or an area sensor. In this case, a first predetermined area of the single line sensor or the area sensor constitutes the first light-receiving element, and a second predetermined area that is different from the first predetermined area constitutes the second light-receiving element.

Furthermore, in case that a position where, for example, the optical spectrum appears is fixed, the first light-receiving element and the second light-receiving element may comprise a plurality of PMTs arranged for each emission line.

In addition, the wavelength of the light emitted from the light source is not limited to the near infrared light of 1100 nm, may be the wavelength of such as 800 nm, 900 nm or 1000 nm. The shape or the characteristics of the first diffraction grating and the second diffraction grating may be appropriately designed to be coincident with the wavelength emitted from the light source.

Furthermore, similar to the OCT device of the first embodiment, in case that the interference light first enters the first diffraction grating and then enters the second diffraction grating, the OCT device may be so arranged that the first diffraction grating diffracts the TE polarization component (p polarization component) as the first polarization component of the interference light, and transmits the TM polarization component (s polarization component) as the second polarization component of the interference light without diffraction. In this case, the second diffraction grating should diffract the TM polarization component of the interference light.

In addition, the second diffraction grating may have a characteristic of diffracting not only the second polarization component of the interference light that is transmitted through the first diffraction grating without diffraction but also the first polarization component. For example, in case that almost all of the first polarization light of the interference light is diffracted by the first diffraction grating, the first polarization component of the interference light scarcely enters the second diffraction grating. As a result of this, even though the second diffraction grating has a characteristic of being able to diffract the first polarization component of the interference light with high efficiency, it is possible for the second light-receiving element to obtain the optical spectrum of the second polarization component of the interference light.

The measurement optical system and the reference optical system are not limited to those described in the first embodiment. For example, each of the reflected light and reference light may enter the optical fiber respectively and be joined by a circulator or the like so that the interference light is emitted to the first diffraction grating.

The object to be measured is not limited to the retina of the eye, and may be a tooth. In addition, the object to be measured is not limited to a biological tissue, and the present claimed invention may be used to obtain a tomographic image of other material. In this case, the wavelength of the light emitted from the light source may be appropriately set in accordance with the transmission or the reflection scattering characteristic of the light of the object to be measured.

The spectroscope in accordance with this invention is not limited to be used for the OCT device, and it may be used for an optical inspection device that conducts some detection based on the optical spectrum of multiple polarization components. The optical inspection device may comprise a spectroscope and a spectrum signal output part that outputs a spectrum signal for each wavelength from at least the first light-receiving element of the spectroscope. For example, the spectrum signal may be output for a single polarization component, or the spectrum signal may be output for a plurality of polarization components. More concretely, the optical inspection device may configure a polarization fluorescent measurement device to measure a reaction of a cell or the like. In addition, as another embodiment of the optical inspection device may be a spectral reflection film thickness meter. In accordance with this arrangement of the spectral reflection film thickness meter, it becomes possible to measure a thickness of a film accurately in a process of film forming of a semiconductor.

In addition, the spectroscope in accordance with this invention is not limited to the spectroscope in accordance with the above-mentioned each embodiment that disperses the interference light for each polarization component. The spectroscope may disperse the light containing the reflected light or the transmitted light from the object to be measured such as the interference light, or may disperse the reflected light itself or the transmitted light itself from the object to be measured.

In addition, the embodiment may be variously modified or combined without departing from a spirit of the invention.

POSSIBLE APPLICATIONS IN INDUSTRY

In accordance with the spectroscope in accordance with this invention, it is possible for the first diffraction grating to separate the incident light into the first polarization component and the second polarization component and to diffract and spectrally disperse the first polarization component of the incident light. As a result of this, unlike a conventional spectroscope, since there is no need of additionally providing a polarization beam splitter to separate the polarization component, it is possible to reduce loss of the light intensity or distortion of a wave surface without increasing a number of a reflecting surface.

The invention claimed is:

1. A spectroscope comprising
a first diffraction grating to which an incident light including at least a transmitted light or a reflected light from an object to be measured enters, which diffracts a first polarization component of the incident light, and which transmits a second polarization component of the incident light without diffraction, the second polarization component of the incident light being different from the first polarization component of the incident light,
a first light-receiving element that receives a spectrum of the first polarization component of the incident light diffracted by the first diffraction grating,
a second diffraction grating to which the second polarization component of the incident light transmitted through the first diffraction grating without diffraction enters and which diffracts the second polarization component of the incident light that is transmitted through the first diffraction grating, and
a second light-receiving element that receives a spectrum of the second polarization component of the incident light diffracted by the second diffraction grating,
wherein the first polarization component of the incident light received by the first light-receiving element does not pass through the second diffraction grating.

2. The spectroscope described in claim 1, wherein each of the first diffraction grating and the second diffraction grating is a transmission type diffraction grating.

3. The spectroscope described in claim 1, and further comprising
a first lens arranged between the first diffraction grating and the first light-receiving element, and
a second lens arranged between the second diffraction grating and the second light-receiving element.

4. The spectroscope described in claim 1, wherein the first polarization component is a TM polarization component and the second polarization component is a TE polarization component.

5. The spectroscope described in claim 1 further comprising
a first lens that is arranged between the first diffraction grating and the first light-receiving element, wherein the spectrum of the first polarization component of the incident light received by the first light-receiving element is condensed by the first lens after being diffracted solely by the first diffraction grating and the second polarization component of the incident light that is transmitted through the first diffraction grating does not pass through the first lens.

6. The spectroscope described in claim 1 further comprising
a first polarizer that is arranged between the first diffraction grating and the first light-receiving element, wherein
the spectrum of the first polarization component of the incident light received by the first light-receiving element is transmitted by the first polarizer after being diffracted solely by the first diffraction grating and the second polarization component of the incident light that is transmitted through the first diffraction grating does not pass through the first polarizer.

7. The spectroscope described in claim 1 further comprising
a polarizer disposed between the first diffraction grating and the second diffraction grating that receives the second polarization component of the incident light transmitted through the first diffraction grating, wherein the first polarization component of the incident light diffracted by the first diffraction grating does not pass through the polarizer.

8. An optical inspection device comprising
the spectroscope described in claim 1, and
a spectrum signal output part that outputs a spectrum signal indicating a distribution for each wavelength based on at least an output signal of the first light-receiving element.

9. An OCT device comprising
the optical inspection device described in claim 8,
an optical fiber mechanism wherein the incident light that enters from a light incident end is emitted from a light emission end to the first diffraction grating,
a light source that emits a near infrared light,
a diverging mechanism that diverges the light that is emitted from the light source into a measurement light and a reference light, a reference optical system that enters the reference light diverged by the diverging mechanism to the light incident end and a measurement optical system that irradiates the measurement light diverged by the diverging mechanism on the object to be measured so as to enter the reflected light that generates on the object to be measured.

10. The OCT device described in claim 9 and further comprising an analysis part that produces a first tomographic image based on the output signal of the first light-receiving element and produces a second tomographic image based on an output from the second light-receiving element.

* * * * *